(12) United States Patent
Friedman et al.

(10) Patent No.: US 7,390,302 B2
(45) Date of Patent: Jun. 24, 2008

(54) METHOD AND SYSTEM OF DETERMINING NIBP TARGET INFLATION PRESSURE USING AN SPO$_2$ PLETHYSMOGRAPH SIGNAL

(75) Inventors: Bruce A. Friedman, Tampa, FL (US); John W. Booth, Tampa, FL (US); Lawrence T. Hersh, Tampa, FL (US)

(73) Assignee: The General Electric Company, Schenectady, NY (US)

( * ) Notice: Subject to any disclaimer, the term of this patent is extended or adjusted under 35 U.S.C. 154(b) by 3 days.

(21) Appl. No.: 11/464,918

(22) Filed: Aug. 16, 2006

(65) Prior Publication Data

US 2008/0045846 A1    Feb. 21, 2008

(51) Int. Cl.
*A61B 5/02* (2006.01)
(52) U.S. Cl. .................. 600/490; 600/493; 600/494; 600/495; 600/483
(58) Field of Classification Search .......... 600/483, 600/485, 490–503, 481, 300, 301
See application file for complete search history.

(56) References Cited

U.S. PATENT DOCUMENTS

| | | | |
|---|---|---|---|
| 4,360,029 A | 11/1982 | Ramsey, III | |
| 4,394,034 A | 7/1983 | Murphy et al. | |
| 4,461,226 A | 7/1984 | Tajima | |
| 4,543,962 A | 10/1985 | Medero et al. | |
| 4,546,775 A | 10/1985 | Medero | |
| 4,638,810 A | 1/1987 | Ramsey, III et al. | |
| 4,754,761 A | 7/1988 | Ramsey, III et al. | |
| 4,776,339 A * | 10/1988 | Schreiber | 600/324 |
| 4,780,824 A * | 10/1988 | Niwa et al. | 600/513 |
| 4,796,184 A | 1/1989 | Bahr et al. | |
| 4,889,133 A | 12/1989 | Nelson et al. | |
| 4,928,701 A * | 5/1990 | Harada et al. | 600/490 |
| 4,949,710 A | 8/1990 | Dorsett et al. | |
| 5,052,397 A | 10/1991 | Ramsey, III et al. | |
| 5,170,795 A | 12/1992 | Ramsey, III et al. | |
| 5,261,414 A * | 11/1993 | Aung et al. | 600/496 |
| 5,267,567 A * | 12/1993 | Aung et al. | 600/493 |
| 5,279,303 A * | 1/1994 | Kawamura et al. | 600/496 |
| 5,309,908 A * | 5/1994 | Friedman et al. | 600/322 |

(Continued)

*Primary Examiner*—Charles A. Marmor, II
*Assistant Examiner*—Navin Natnithithadha
(74) *Attorney, Agent, or Firm*—Andrus, Sceales, Starke & Sawall, LLP

(57) ABSTRACT

A method and system for operating a non-invasive blood pressure monitor that utilizes an SpO$_2$ plethysmograph signal to determine the initial inflation pressure for the blood pressure cuff of the NIBP monitor. A pulse sensor is placed on the patient's limb distal to the blood pressure cuff such that as the blood pressure cuff is inflated, the pulse signals from the pulse sensor will be reduced. When the blood pressure cuff reaches systolic pressure, the pulse signals from the pulse sensor will be initially attenuated and eventually eliminated, thus providing an indication that the cuff pressure has reached systolic pressure for the patient. The central processor of the NIBP monitor compares the pulse signals during cuff inflation to an average pulse signal and terminates the inflation of the blood pressure cuff upon sufficient attenuation. The use of the SpO$_2$ plethysmograph signal to determine the initial inflation pressure reduces both the over-inflation of the blood pressure cuff and the under-inflation of the blood pressure cuff which increases the rate at which the blood pressure measurement can be made while increasing patient comfort.

17 Claims, 5 Drawing Sheets

U.S. PATENT DOCUMENTS

| | | |
|---|---|---|
| 5,577,508 A | 11/1996 | Medero |
| 5,579,776 A | 12/1996 | Medero |
| 5,590,662 A | 1/1997 | Hersh et al. |
| 5,704,362 A | 1/1998 | Hersh et al. |
| 5,730,139 A * | 3/1998 | Miyazaki et al. ............ 600/493 |
| 5,743,857 A * | 4/1998 | Shinoda et al. ............ 600/496 |
| 5,830,149 A * | 11/1998 | Oka et al. .................. 600/500 |
| 5,836,887 A * | 11/1998 | Oka et al. .................. 600/494 |
| 5,865,756 A * | 2/1999 | Peel, III .................... 600/490 |
| 5,921,936 A * | 7/1999 | Inukai et al. ............... 600/490 |
| 6,007,492 A * | 12/1999 | Goto et al. ................. 600/485 |
| 6,027,455 A * | 2/2000 | Inukai et al. ............... 600/490 |
| 6,036,651 A * | 3/2000 | Inukai et al. ............... 600/485 |
| 6,241,680 B1 * | 6/2001 | Miwa ........................ 600/494 |
| 6,251,081 B1 * | 6/2001 | Narimatsu .................. 600/490 |
| 6,358,213 B1 | 3/2002 | Friedman et al. |
| 6,423,010 B1 | 7/2002 | Friedman et al. |
| 6,440,080 B1 | 8/2002 | Booth et al. |
| 6,491,638 B2 * | 12/2002 | Oka .......................... 600/494 |
| 6,589,183 B2 * | 7/2003 | Yokozeki .................... 600/485 |
| 6,602,198 B2 * | 8/2003 | Yokozeki .................... 600/485 |
| 6,645,154 B2 * | 11/2003 | Oka .......................... 600/485 |
| 2002/0052552 A1 * | 5/2002 | Yokozeki .................... 600/481 |
| 2002/0082507 A1 | 6/2002 | Kolluri et al. |

* cited by examiner

US 7,390,302 B2

METHOD AND SYSTEM OF DETERMINING NIBP TARGET INFLATION PRESSURE USING AN SPO₂ PLETHYSMOGRAPH SIGNAL

FIELD OF THE INVENTION

The present invention relates to a method of operating an automated blood pressure measuring apparatus. More specifically, the present invention relates to a method of operating an automated non-invasive blood pressure (NIBP) monitor that utilizes a separate pulse monitor to enhance the performance of the NIBP monitor.

BACKGROUND OF THE INVENTION

Automated blood pressure monitoring has rapidly become an accepted and, in many cases, essential aspect of human healthcare. Such monitors are now a conventional part of the patient environment in emergency rooms, intensive and critical care units, and in the operating theater.

The oscillometric method of measuring blood pressure involves applying an inflatable cuff around an extremity of a patient's body, such as a patient's upper arm. The cuff is inflated to a pressure above the patient's systolic pressure and then the cuff pressure is reduced either continuously or incrementally in a series of small steps. A pressure sensor measures the cuff pressure, including the cuff pressure fluctuations resulting from the heart pumping activity that then causes pressure or volume oscillations in the artery under the cuff. The data from the pressure sensor is used to compute the patient's systolic pressure, mean arterial pressure (MAP) and diastolic pressure.

An example of the oscillometric method of measuring blood pressure is shown and described in U.S. Pat. Nos. 4,360,029; 4,394,034; and 4,638,810, which are commonly assigned with the present invention.

During the use of a conventional NIBP monitoring system, the blood pressure cuff is placed around the arm of a patient and is inflated to a pressure that fully occludes the brachial artery to prevent blood flow. The cuff is then progressively deflated and a pressure transducer detects pressure pulses as blood begins to flow past the pressure cuff. As can be understood, the selection of the initial inflation pressure determines the amount of time and deflation required before the NIBP system begins to detect cuff oscillations and blood flow. If the initial inflation pressure is selected well above the systolic blood pressure for the patient, the NIBP system over inflates the blood pressure cuff, resulting in patient discomfort and extended measurement time. Alternatively, if the initial inflation pressure is selected below the systolic blood pressure for the patient, the blood pressure cuff must re-inflate to obtain an accurate reading. Therefore, it is desirable to inflate the blood pressure cuff slightly above the systolic pressure to enhance the performance of the NIBP monitoring system.

SUMMARY OF THE INVENTION

The following describes a method and system for monitoring the blood pressure in a patient that utilizes the output of a pulse monitor, such as the SpO₂ plethysmograph waveform from an SpO₂ monitor, to improve the performance of a non-invasive blood pressure (NIBP) monitor. The NIBP monitor includes a blood pressure cuff that is placed upon the limb of a patient, such as the arm. The blood pressure cuff is selectively inflated and deflated by a central processor, which controls the availability of pressurized air to the cuff and the position of valves that release air from the cuff. During the deflation of the blood pressure cuff from an initial inflation pressure, oscillation pulses are detected and the central processor calculates a pulse amplitude for each oscillation pulse, such that the pulse amplitudes are utilized to calculate the blood pressure of a patient.

The combined system further includes a pulse monitor having a pulse sensor that delivers a continuous waveform, including a series of spaced pulses each representing a beat of the patient's heart, to the central processor of the NIBP monitor. Preferably, the pulse monitor is a pulse oximeter monitor having a finger probe sensor positioned on the finger of the patient. The finger probe sensor must be placed upon the finger of the patient on the same arm of the patient that includes the blood pressure cuff of the NIBP monitor. The pulse oximeter monitor delivers a plethysmographic waveform to the central processor of the NIBP monitor that includes a series of spaced pulse signals each corresponding to a heartbeat of the patient.

During operation of the NIBP monitor, the central processor inflates the blood pressure cuff as quickly as possible to a pre-determined target inflation pressure. During the initial inflation of the blood pressure cuff, the central processor monitors the pulse signals received from the pulse monitor. Since the sensor of the pulse monitor is positioned on the same arm as the blood pressure cuff, as the blood pressure cuff approaches the systolic blood pressure for the patient, the pressure signals from the pressure sensor become attenuated due to the lack of blood flow past the blood pressure cuff.

As the pressure signals become attenuated, the central processor of the NIBP monitor compares the attenuated pulse signals to a normal pulse signal. The central processor terminates inflation of the blood pressure cuff when the difference between the attenuated pulse signals and the normal pulse signals exceeds a threshold value. The threshold value for the difference between the attenuated pulse signals and normal pulse signals can be based upon the amplitude of the pulse signals, the rate of change of the base signal or another value associated with the individual pulse signals. The pressure at which the blood pressure cuff inflation is terminated is the initial inflation pressure for the algorithm used to operate the NIBP monitor. Since the initial inflation pressure is based upon the pulses from the plethysmographic waveform, the initial inflation pressure may be set above the predicted target inflation pressure or below the predicted target inflation pressure, depending upon the individual patient. Thus, the optimal initial inflation pressure is based upon measurements taken during the inflation of the blood pressure cuff, rather than estimates calculated before beginning the blood pressure monitoring process.

BRIEF DESCRIPTION OF THE DRAWINGS

The drawings illustrate the best mode presently contemplated of carrying out the invention. In the drawings.

DETAILED DESCRIPTION OF THE INVENTION

Figure 1:
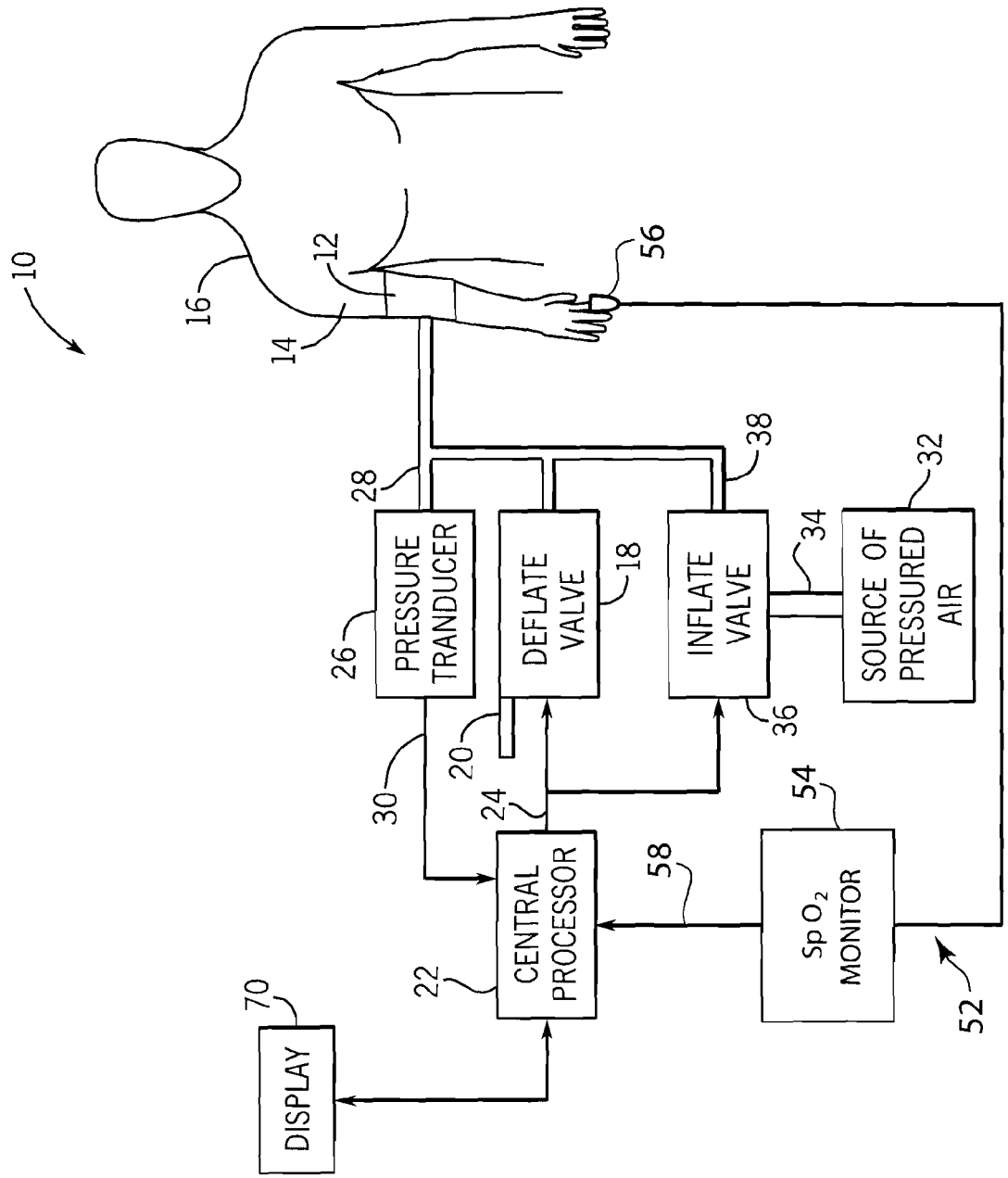
FIG. 1 is a block diagram of a system for monitoring blood pressure in a patient using an NIBP monitor and a pulse monitor.

FIG. 1 generally illustrates a non-invasive blood pressure (NIBP) monitoring system 10 of conventional construction. The NIBP monitoring system 10 includes a blood pressure cuff 12 placed on the arm 14 of a patient 16. The blood pressure cuff 12 can be inflated and deflated for occluding the brachial artery of the patient 16 when in the fully inflated condition. As the blood pressure cuff 12 is deflated using the deflate valve 18 having exhaust 20, the arterial occlusion is gradually relieved. The deflation of the blood pressure cuff 12 by the deflate valve 18 is controlled by a central processor 22 through the control line 24.

A pressure transducer 26 is coupled by duct 28 to the blood pressure cuff 12 for sensing the pressure within the cuff 12. In accordance with conventional oscillometric techniques, the pressure transducer 26 is used to sense pressure oscillations in the cuff 12 that are generated by pressure changes in the brachial artery under the cuff. The electrical oscillation pulses from the pressure transducer 26 are obtained by the central processor 22, using an analog-to digital converter, through connection line 30.

A source of pressurized air 32, such as an air compressor or compressed gas cylinder, is connected by duct 34. In an embodiment incorporating an air compressor, the air compressor is coupled directly to the duct 38. However, if the source of pressurized air is supplied by a compressed gas cylinder, an inflate valve 36 is positioned between the source 32 and the duct 38. The operation of the inflate valve 36 is controlled by the central processor 22 through the control line 24. Thus, the inflation and deflation of the blood pressure cuff 12 is controlled by the central processor 22 through the deflate valve 18 and the inflate valve 36, respectively.

From the standpoint of the principles of the present invention, the processing of the oscillation signals from first pressure transducer 26 by the central processor 22 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al in U.S. Pat. No. 4,543,962, of Medero in U.S. Pat. No. 4,546,775, of Hood, Jr. et al in U.S. Pat. No. 4,461,266, of Ramsey, III et al in U.S. Pat. No. 4,638,810, of Ramsey III et al in U.S. Pat. No. 4,754,761, of Ramsey III et al in U.S. Pat. No. 5,170,795, of Ramsey III et al in U.S. Pat. No. 5,052,397, of Medero in U.S. Pat. No. 5,577,508 and of Hersh et al in U.S. Pat. No. 5,590,662, all of which are commonly assigned herewith and the disclosures of which are hereby incorporated by reference. In any event, it is desirable to use any of the known techniques to determine the quality of the oscillation complexes received at each cuff pressure so that the blood pressure determination is made using the physiological relevant cuff pressure oscillations from each heartbeat and not artifacts.

Figure 2:
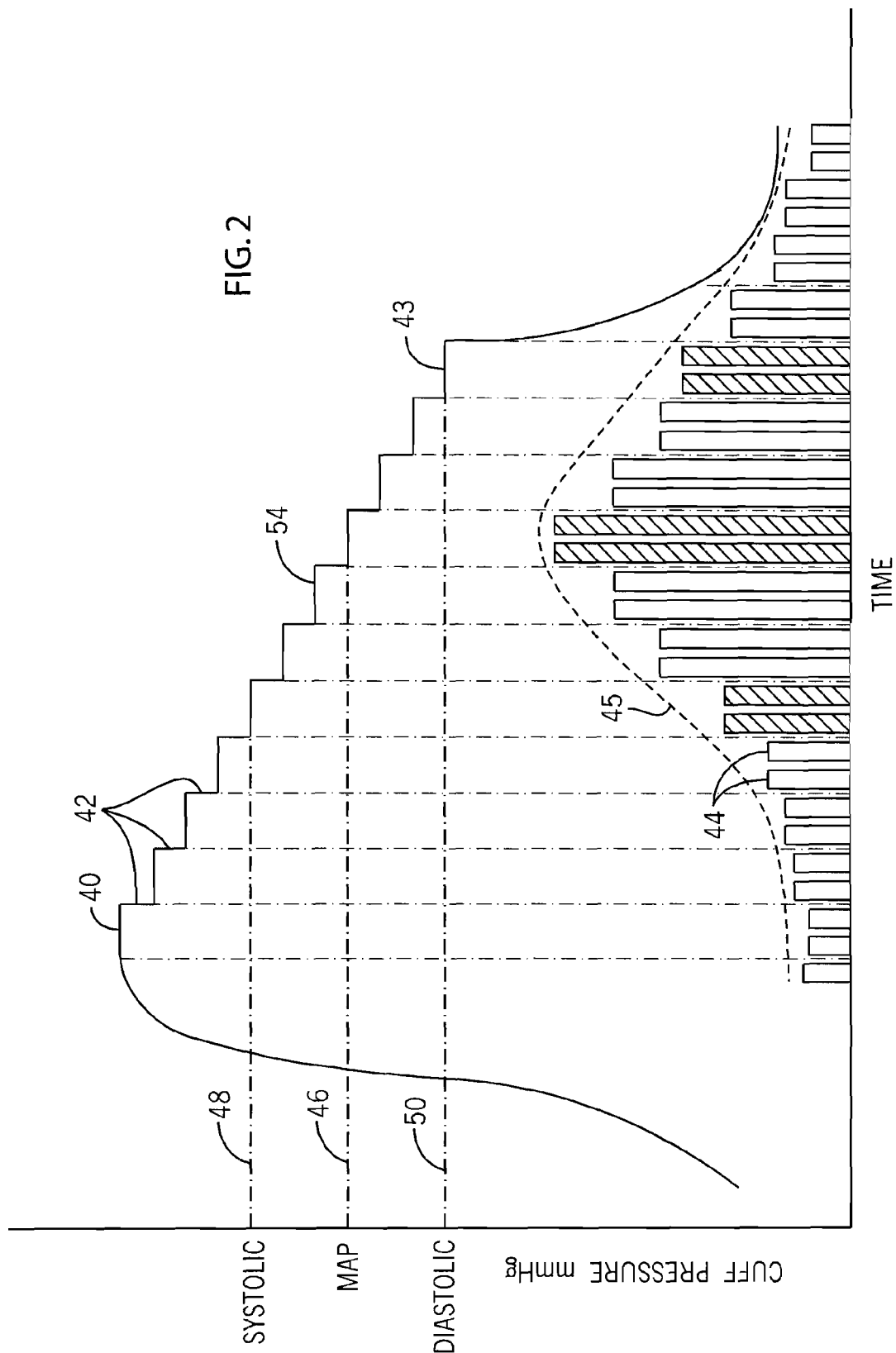
FIG. 2 is a graph depicting one method of operating an NIBP monitor by obtaining two oscillation pulse amplitudes at each of a series of pressure steps.

During normal operation of the NIBP monitoring system 10 shown in FIG. 1, the blood pressure cuff 12 is initially placed on the patient 16, typically around the subject's upper arm 14 over the brachial artery. At the inception of the measuring cycle, the blood pressure cuff 12 is inflated to a target inflation pressure that fully occludes the brachial artery, i.e., prevents blood from flowing through the brachial artery at any time in the heart cycle. In FIG. 2, the target inflation pressure is illustrated by reference number 40.

After the blood pressure cuff has been inflated to the target inflation pressure 40, the deflate valve is actuated by the central processor to deflate the cuff in a series of pressure steps 42. Although various values for each pressure step 42 can be utilized, in an exemplary example, each pressure step 42 is typically about 8 mmHg per step.

After each pressure step 42, the NIBP monitoring system detects and records the amplitude 44 of two cuff oscillation pulses for the current cuff pressure level. The pressure transducer measures the internal cuff pressure and provides an analog signal characterizing the blood pressure oscillatory complexes. The peak values of the complex signals are determined within the central processor.

As the cuff pressure decreases from the initial inflation pressure, the NIBP monitoring system detects the cuff pressure oscillations 44 and records the pressure oscillation amplitudes for the current cuff pressure. The central processor within the NIBP monitoring system can then calculate the MAP 46, systolic pressure 48 and diastolic pressure 50.

As the measurement cycles progress, the peak amplitude of the oscillation pulses generally become monotonically larger to a maximum and then become monotonically smaller as the cuff pressure continues toward full deflation, as illustrated by the bell-shaped graph 45 in FIG. 2. The peak amplitude of the cuff pressure oscillation complexes, and the corresponding occluding-cuff pressure values, are retained in the central processor memory. The oscillometric measurements are used by the central processor to calculate the mean arterial pressure (MAP) 46, the systolic pressure 48 and the diastolic pressure 50 in a known manner. The calculated blood pressure measurements are viewable on the display 70 shown in FIG. 1, Referring back to FIG. 1, the system of the present invention further includes a pulse monitor 52 for detecting pulse signals from the patient indicative of the patient's heartbeat. In the embodiment of the invention illustrated in FIG. 1, the pulse monitor 52 is a pulse oximeter monitoring system 54 having a sensor that detects a plethysmographic signal from the patient, such as a finger probe 56 positioned on the patient 16 to determine the $SpO_2$ level of the patient 16.

The pulse oximeter monitoring system 54 generates an $SpO_2$ plethysmographic signal that is provided to the central processor 22 of the NIBP monitoring system 10 through a communication line 58. In addition to providing the $SpO_2$ level for the patient, the pulse oximeter monitor 54 provides a plethysmographic waveform 60 (FIG. 3) that includes a series of pulses 62 that each result from a beat of the patient's heart. Since the finger probe 56 is attached to the patient 16 at all times, the pulse oximeter monitor 54 continuously monitors the patient and generates a continuous plethysmographic waveform 60 having the series of time-spaced pulses 62.

Although a pulse oximeter monitor 54 is shown and described in the preferred embodiment of FIG. 1, it should be understood that other types of pulse monitoring systems and sensors can be utilized while operating within the scope of the invention. As an example, an impedance plethysmograph monitor can be placed on the finger or wrist, a piezoelectric sensor could be utilized on the wrist of the patient or any other means of sensing the blood volume pulse within the patient and distal to the blood pressure cuff can be utilized while operating within the scope of the present invention.

Figure 3:
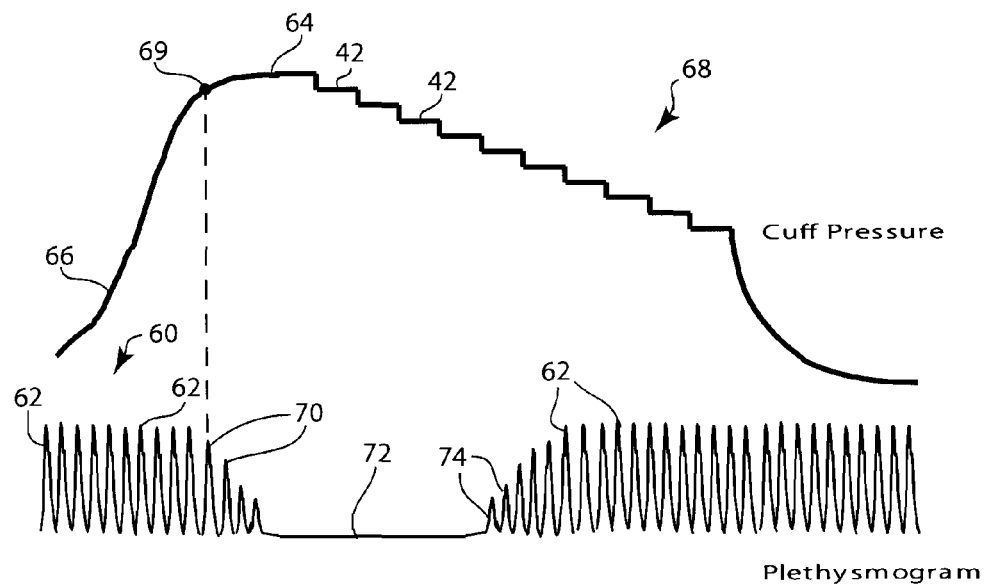
FIG. 3 illustrates the plethysmographic waveform from the pulse monitor as the blood pressure cuff of the NIBP monitor is inflated to a target inflation pressure.

Referring now to FIG. 3, prior to beginning operation of the NIBP monitoring system to determine the patient blood pressure, the pulse sensor within the finger probe detects a series of individual pulses 62 that each result from a beat of the patient's heart. The continuous plethysmograph signal 60 from the finger probe is obtained by the SpO$_2$ monitor 54 and relayed to the central processor 22 of the NIBP monitoring system 10, as illustrated in FIG. 1.

When the NIBP monitoring system begins operation, the blood pressure cuff 12 positioned on the arm of the patient is rapidly inflated from a very low pressure to a target inflation pressure 64, as indicated by the steeply sloped portion 66 of the cuff pressure profile 68 of FIG. 3. Since the blood pressure cuff and the finger probe are positioned on the same arm of the patient, as the cuff pressure increases near and above the systolic pressure for the patient, as shown by pressure level 69, the amplitude of the pulse signals 62 begins to decrease, as shown by the attenuated pulses 70 in FIG. 3. Once the cuff pressure exceeds the systolic pressure for the patient, the blood flow through the brachial artery past the blood pressure cuff is terminated such that the pulse signals are no longer present in the plethysmograph signal 60, as illustrated by the flat portion 72 of the plethysmograph signal 60.

Once the cuff pressure 68 decreases below the systolic blood pressure through the series of pressure steps 42 to allow blood to flow past the blood pressure cuff, the flat portion 72 terminates and attenuated pulse signals 74 return until the complete blood flow returns and the full size pulse signals 62 are again present within the plethysmograph signal 60. As can be understood in FIG. 3, the pressure at which the pulse signals 62 begin to become attenuated is an indication that the blood pressure cuff has been inflated to a pressure sufficient to restrict the flow of blood past the blood pressure cuff, as detected by the sensor within the finger probe 56. Thus, once the pulse signals have been sufficiently attenuated, inflation of the blood pressure cuff can be terminated, since the cuff pressure is above the systolic pressure for the patient. As can be understood in FIG. 1, the finger probe 56 must be placed at the same arm of the patient as the blood pressure cuff 12 to detect the attenuated pulse signals upon inflation of the blood pressure cuff 12.

Figure 4:
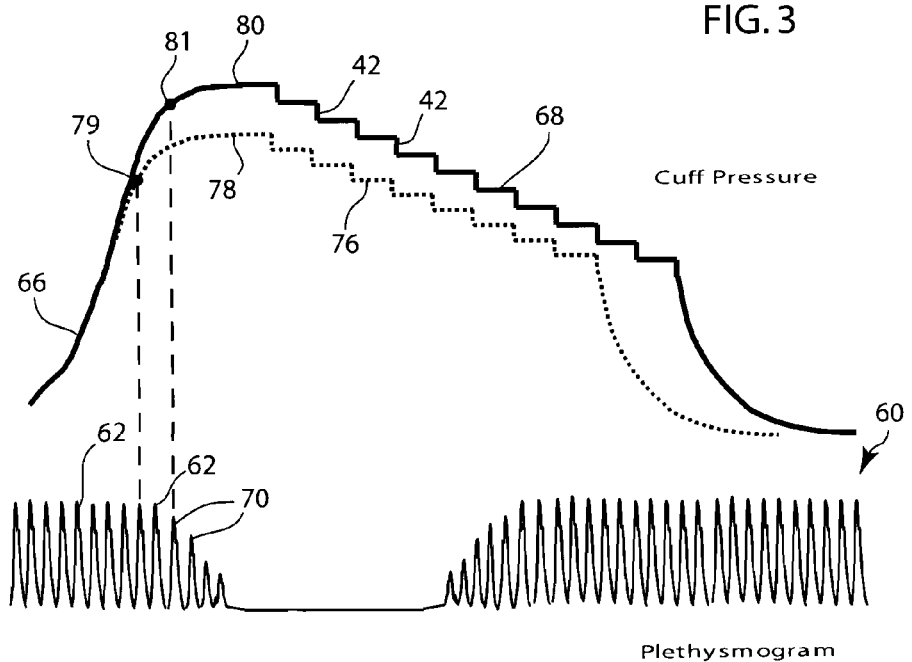
FIG. 4 is a graphical illustration of the plethysmographic waveform and the adjusted initial inflation pressure of the blood pressure cuff.

Referring now to FIG. 4, thereshown is a first operational example utilizing the method and system of the present invention. The dashed line shown in FIG. 4 represents an estimated cuff inflation curve 76 predicted by the central processor of the NIBP monitoring system. The predicted curve 76 included a target inflation pressure 78 that is predetermined by the central processor based upon a typical patient before beginning the blood pressure determination procedure. The selection of the target inflation pressure 78 is oftentimes difficult for the NIBP monitoring system during the first iteration of determining the patient's blood pressure since the NIBP monitoring system does not have any previous blood pressure measurement values for the specific patient upon which to base an estimation for the target inflation pressure 78. Further, since the NIBP monitoring system may be moved from patient to patient within a hospital or critical care environment, the selection of the target inflation pressure is typically a standard value and is not patient-dependent.

FIG. 4 illustrates a situation in which the predicted target inflation pressure 78 is too low for the individual patient. As illustrated, as the cuff pressure 68 increases during the sloped initial inflation portion 66, the amplitude of each of the pulse signals 62 remains generally constant, even as the cuff pressure 68 reaches the inflation termination point 79, at which time the cuff inflation ceases to inflate the cuff to the target inflation pressure 78. Since the pulse signals 62 do not decrease in amplitude even when the cuff pressure reaches the target inflation pressure 78, the cuff pressure has not yet reached the systolic pressure for the patient. Since the systolic pressure has not been reached by the target inflation pressure 78, the central processor continues to inflate the blood pressure cuff until the central processor detects the attenuated pulses 70.

Once the attenuated pulses are detected, the inflation of the blood pressure cuff is terminated at point 81 and the cuff reaches an initial inflation pressure 80. In the example illustrated in FIG. 4, the initial inflation pressure 80 is well above the target inflation pressure 78. If the NIBP monitoring system were operated utilizing only the target inflation pressure 78, the inflation pressure of the blood pressure cuff would have been insufficient and the blood pressure cuff would have needed to be re-inflated to a higher pressure target pressure to obtain an accurate blood pressure reading. However, by utilizing the plethysmograph signal 60, the NIBP monitoring system automatically increased the initial inflation pressure of the blood pressure cuff until the central processor detected the beginning of attenuated pulse signals. After reaching the initial inflation pressure 80, the cuff pressure is decreased in the series of pressure steps 42 and the blood pressure is determined utilizing oscillation pulse amplitudes in the known manner described previously.

Figure 5:
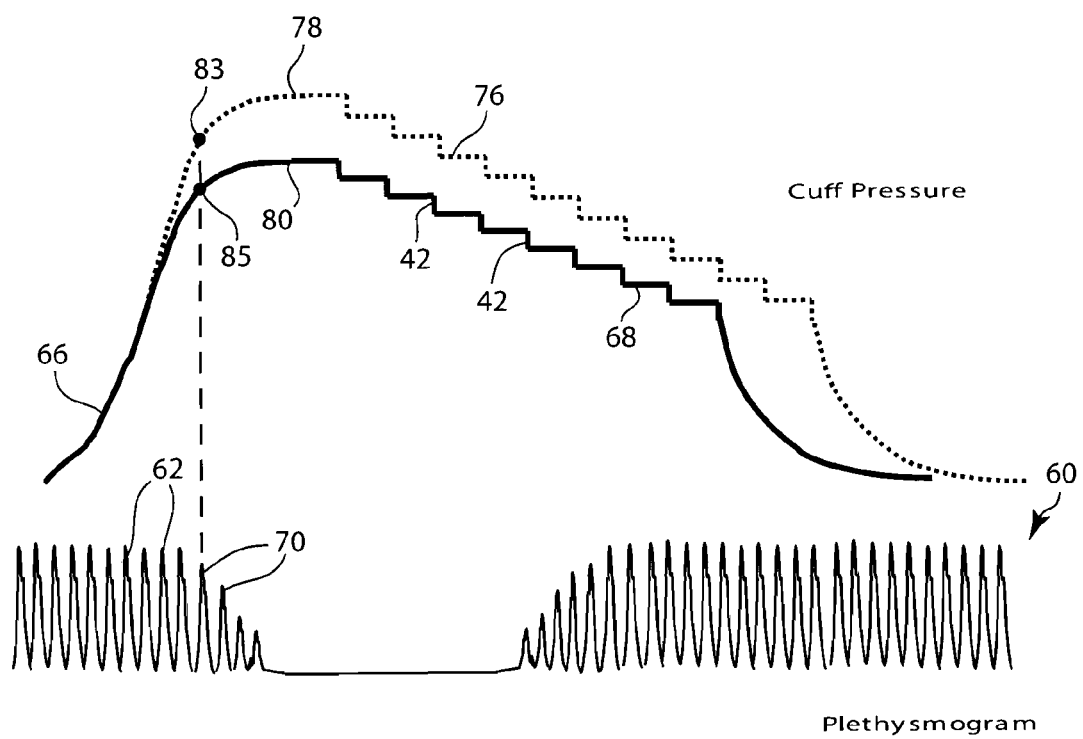
FIG. 5 is a graphical illustration of the plethysmographic waveform and the adjusted initial inflation pressure of the blood pressure cuff.

Referring now to FIG. 5, thereshown is an example of the operation of the combined NIBP monitoring system when the predicted target inflation pressure 78 is too high for the individual patient. In the embodiment illustrated in FIG. 5, the predicted cuff inflation profile 76 is again shown in dashed lines. Like the embodiment illustrated in FIG. 4, the central processor of the NIBP monitoring system initially predicts the target inflation pressure 78. However, as the cuff pressure 68 increases during the sloped portion 66 and reaches point 83, the pulse signals 62 begin to attenuate at a cuff pressure well below the target inflation pressure 78, as shown by the attenuated pulses 70. When the central processor 22 detects the attenuated pulses 70 before the cuff pressure reaches the predicted target inflation pressure 78, the central processor terminates the inflation of the blood pressure cuff at point 85 to define the initial inflation pressure 80.

In the example illustrated in FIG. 5, the initial inflation pressure 80 is well below the target inflation pressure 78. If the NIBP monitoring system utilized the target inflation pressure 78, the blood pressure cuff would be over-inflated, leading to patient discomfort and increased time required to obtain a blood pressure measurement. As discussed previously, once the blood pressure cuff reaches the initial inflation pressure 80, the cuff pressure is reduced in the series of pressure steps 42 and the oscillation pulse amplitudes are utilized to calculate a blood pressure estimate for the patient in accordance with known methods.

As discussed above in the two examples shown in FIGS. 4 and 5, the central processor 22 of the NIBP monitoring system 10 terminates the inflation of the blood pressure cuff upon detection of the attenuated pulse signals 70. The determination of when the pulse signals have been attenuated a sufficient amount to indicate that the blood pressure cuff has been properly inflated can be based upon various properties of the individual pulse signals 62 as compared to the attenuated pulses 70. As an example, the inflation of the blood pressure cuff could be terminated when the amplitude of the attenuated signals fall a selected percentage below the amplitude of the standard pulse signals 62. Alternatively, the comparison could be based upon a rate of change of the pulse amplitudes relative to the normal pulse signals 62. Further, the decision to terminate inflation of the blood pressure cuff could also be based upon the rate of change of the baseline signal during the inflation of the blood pressure cuff. As illustrated in FIG. 5, the plethysmograph signal 60 includes a DC baseline component as well as the oscillating AC components created by the pulses resulting from the heartbeat of the patient. As the blood pressure cuff occludes the brachial artery, the DC baseline component of the plethysmograph signal 60 also decreases in addition to the amplitude attenuation of the individual pulse signals 62. Although the decision to stop the inflation of the blood pressure cuff could be based upon an amplitude measurement of the pulse signals and the rate of change of the baseline signal, it is also contemplated that other pulse parameters could be utilized while operating within the scope of the present invention.

Figure 6:
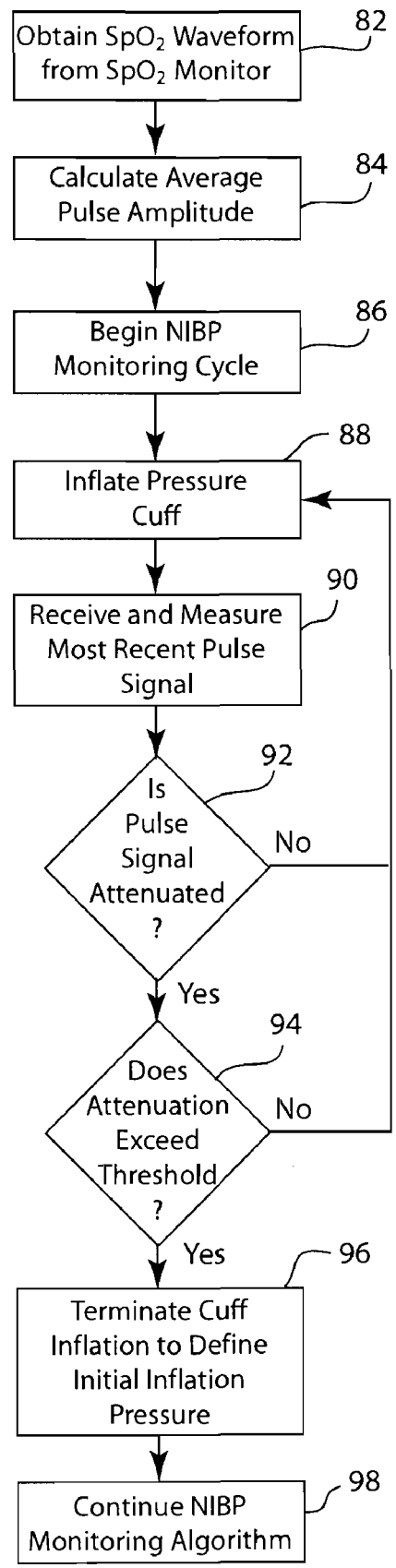
FIG. 6 is a flowchart illustrating the operational sequence utilized by the system and method of the present invention to determine the blood pressure of a patient using an NIBP monitor and a pulse oximeter monitor.

FIG. 6 illustrates a flowchart of the operational sequence of the NIBP monitoring system in accordance with the one embodiment of the present invention. As illustrated in FIG. 6, the NIBP monitoring system continuously receives a plethysmographic waveform from the pulse monitor, as illustrated in step 82. The central processor of the NIBP monitoring system receives the continuous waveform and calculates an average pulse amplitude for the pulse signals based upon a series of past pulse signals in step 84. The average pulse amplitude is used by the central processor to detect when the amplitude of the pulse signals become attenuated during the inflation of the blood pressure cuff.

After the average pulse amplitude has been calculated, the central processor begins the normal NIBP monitoring cycle in step 86 by inflating the blood pressure cuff in step 88. As shown in FIG. 3, the blood pressure cuff is initially inflated along the steeply sloped portion 66 from a nearly zero pressure level to a target inflation pressure. As the blood pressure cuff is inflated, the central processor receives the continuous plethysmographic signal from the SpO$_2$ monitor. As the blood pressure cuff is inflated, the central processor receives and measures the most recent pulse signal from the pulse monitor in step 90.

Upon receiving the most recent pulse signal, the central processor determines whether the pulse signal is attenuated in step 92 as compared to the average pulse amplitude determined in step 84. If the pulse is not attenuated, the central processor returns to step 88 and continues to inflate the blood pressure cuff. However, if the pulse signal is attenuated, the processor then determines in step 94 whether the attenuation exceeds a threshold. As described previously, the attenuation threshold could be based upon the amplitude of each pulse signal or could be based upon the attenuation of the baseline signal included in the plethysmograph signal.

If the central processor determines that the attenuation threshold has been exceeded, the central processor terminates the inflation of the blood pressure cuff in step 96 to define an initial inflation pressure. As illustrated in FIGS. 4 and 5, the initial inflation pressure 80 may be above or below the target inflation pressure 78 selected by the central processor. The use of the plethysmograph signal 60 to set the initial inflation pressure 80 allows the NIBP monitoring system to optimally set the initial inflation pressure based upon information gathered during the inflation of the blood pressure cuff, rather than an estimate calculated prior to the initiation of the NIBP monitoring cycle. Once the cuff pressure has been set at the initial inflation pressure, the central processor operates in accordance with a known NIBP monitoring algorithm to detect oscillation pulse amplitudes and calculate the blood pressure of the patient.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of monitoring blood pressure in a patient, the method comprising the steps of:
   providing a pulse monitor having a sensor operable to detect pulse signals due to the patient's heartbeat;
   positioning a blood pressure cuff on the patient, the blood pressure cuff being operable to restrict a blood flow past the blood pressure cuff;
   positioning the sensor on the patient distal to the blood pressure cuff to detect pulse signals from the patient in the blood flow past the blood pressure cuff;
   inflating the blood pressure cuff to restrict the blood flow;
   monitoring for the presence of the pulse signals from the pulse monitor during inflation of the blood pressure cuff;
   terminating the inflation of the blood pressure cuff based upon the pulse signals to define an initial inflation pressure;
   decreasing the pressure in the blood pressure cuff from the initial inflation pressure while monitoring for oscillation pulses from the blood pressure cuff; and
   calculating the systolic pressure, mean arterial pressure and diastolic pressure for the patient based upon the oscillation pulses detected during the deflation of the blood pressure cuff.

2. The method of claim 1 wherein the pulse monitor sensor is positioned on a finger of the patient.

3. The method of claim 2 wherein the pulse monitor is an SpO$_2$ monitor and thesensor is an SpO$_2$ sensor positioned on the finger of the patient.

4. The method of claim 2 wherein the inflation of the blood pressure cuff isterminated upon the absence of the pulse signals.

5. The method of claim 2 wherein the inflation of the blood pressure cuff isterminated based upon the attenuation of the amplitude of the pulse signals during the inflation of the blood pressure cuff.

6. The method of claim 2 further comprising the steps of:
   calculating an average pulse amplitude for the pulse signals received from the patientprior to inflation of the blood pressure cuff;
   determining the amplitude of each pulse signal during inflation of the blood pressure cuff; and
   terminating the inflation of the blood pressure cuff when the difference between the average pulse amplitude and the amplitude of at least one of the pulse signals detected during inflation exceeds a threshold value.

7. The method of claim 6 wherein the pulse monitor is an SpO$_2$ monitor and thesensor is an SpO$_2$ sensor positioned on a finger of the patient.

8. The method of claim 1 further comprising the step of modifying the rate of the blood pressure cuff inflation based upon the rate of change of the pulse signals.

9. A method of operating a non-invasive blood pressure (NIBP) monitor having a central processor, a blood pressure cuff positionable on an arm of the patient and a pressure transducer operable to detect oscillation pulses beneath the blood pressure cuff, the method comprising the steps of:
   providing a pulse monitor having a sensor positioned to detect pulse signals from the patient representative of the patient's heartbeat;
   positioning a blood pressure cuff on an arm of the patient;

positioning the sensor of the pulse monitor on the same arm of the patient as the blood pressure cuff and anatomically distal to the blood pressure cuff;

inflating the blood pressure cuff to begin to occlude an artery in the arm of the patient;

monitoring for the presence of the pulse signals from the pulse monitor during the inflation of the blood pressure cuff;

terminating the inflation of the blood pressure cuff based upon characteristics of the pulse signals from the pulse monitor to define an initial inflation pressure for the blood pressure cuff;

decreasing the pressure in the blood pressure cuff from the initial inflation pressure while monitoring for oscillation pulses from the pressure transducer; and calculating the systolic pressure, mean arterial pressure and diastolic pressure for the patient based upon the cuff oscillation pulses detected during the deflation of the blood pressure cuff.

10. The method of claim 9 wherein the central processor of the NIBP monitor is in communication with the pulse monitor such that the central processor monitors for the presence of the pulse signals from the pulse monitor.

11. The method of claim 10 wherein each of the pulse signals has a pulse amplitude, wherein the inflation of the blood pressure cuff is terminated based upon a decrease in the pulse amplitude of the pulse signals.

12. The method of claim 9 further comprising the steps of:

receiving a series of pulse signals prior to inflation of the blood pressure cuff;

determining an average pulse signal amplitude for the series of pulse signals received prior to inflation of the blood pressure cuff;

determining a pulse amplitude for each of the pulse signals received during the inflation of the blood pressure cuff; and terminating the inflation of the blood pressure cuff when the pulse signal amplitude of at least one of the pulse signals detected during inflation falls below the average pulse amplitude by a threshold value.

13. The method of claim 9 wherein the pulse monitor is an $SpO_2$ monitor and the sensor is an $SpO_2$ finger probe.

14. The method of claim 9 wherein the characteristic of the pulse signal is the presence of the pulse signal.

15. The method of claim 9 wherein the central processor defines a target inflation pressure for the patient, the method further comprising the steps of:

inflating the blood pressure cuff to the target inflation pressure;

reducing the target inflation pressure upon the absence of pulse signals prior to inflation of the blood pressure cuff to the target inflation pressure; and increasing the target inflation pressure upon the presence of pulse signals when the blood pressure cuff is inflated to the target inflation pressure.

16. A system for determining the blood pressure of a patient, comprising:

a non-invasive blood pressure (NIBP) monitor including a central processor and a display;

a blood pressure cuff positionable on the patient, the blood pressure cuff being selectively inflatable and deflatable by the NIBP monitor;

a pressure transducer operable to measure the pressure within the blood pressure cuff and coupled to the central processor, the pressure transducer being operable to detect oscillation pulses from the patient; and a pulse monitoring system having a sensor positionable on the patient to detect pulse signals from the patient due to the patient's heartbeat, wherein the central processor controls the initial inflation of the blood pressure cuff to and initial inflation pressure based upon the pulse signals received from the pulse monitor.

17. The system of claim 16 wherein the pulse monitor is an $SpO_2$ monitor having a finger probe.

* * * * *